(12) United States Patent
Li et al.

(10) Patent No.: US 11,938,244 B2
(45) Date of Patent: Mar. 26, 2024

(54) METHODS FOR IMPROVING MECHANICAL PROPERTY AND BIOLOGICAL STABILITY OF MAGNESIUM ALLOY AND MANUFACTURING MATERIAL AND APPLICATIONS

(71) Applicant: Hejie Li, Tangshan (CN)

(72) Inventors: Hejie Li, Tangshan (CN); Tianfang Wang, Mountain creek (AU); Xiaosong Liu, Tarragindi (AU); Guoying Ni, Annerley (AU)

(73) Assignee: Hejie Li, Tangshan (CN)

( * ) Notice: Subject to any disclaimer, the term of this patent is extended or adjusted under 35 U.S.C. 154(b) by 0 days.

(21) Appl. No.: 17/905,456

(22) PCT Filed: Feb. 25, 2021

(86) PCT No.: PCT/CN2021/000030
§ 371 (c)(1),
(2) Date: Sep. 1, 2022

(87) PCT Pub. No.: WO2021/174998
PCT Pub. Date: Sep. 10, 2021

(65) Prior Publication Data
US 2023/0146612 A1    May 11, 2023

(30) Foreign Application Priority Data

Mar. 3, 2020   (CN) .......................... 202010140864.9
Apr. 14, 2020  (CN) .......................... 202010291833.3

(51) Int. Cl.
*A61L 27/04* (2006.01)
*A61L 27/34* (2006.01)
(Continued)

(52) U.S. Cl.
CPC ............. *A61L 27/047* (2013.01); *A61L 27/34* (2013.01); *B24B 27/033* (2013.01); *C22F 1/02* (2013.01);
(Continued)

(58) Field of Classification Search
CPC .................................. A61L 27/047; C22F 3/00
See application file for complete search history.

(56) References Cited

FOREIGN PATENT DOCUMENTS

| CN | 101264351 A | 9/2008 |
|----|-------------|--------|
| CN | 104302798 A | 1/2015 |

(Continued)

OTHER PUBLICATIONS

International Search Report issued for International Patent Application No. PCT/CN2021/000030, dated May 24, 2021, 5 pages including English translation.
(Continued)

*Primary Examiner* — Dah-Wei D. Yuan
*Assistant Examiner* — Andrew J Bowman
(74) *Attorney, Agent, or Firm* — Hamre, Schumann, Mueller & Larson, P.C.

(57) ABSTRACT

A heat treatment method for improving the mechanical property and the biofunctional stability of a magnesium alloy is provided, comprising: (1) fully annealing an original cold-drawn magnesium alloy AZ31; (2) polishing a surface of the magnesium alloy AZ31 from the step (1) by a waterproof abrasive paper; (3) heating the magnesium alloy AZ31 obtained from the step (2) to a temperature of 330° C. to 350° C. and keeping the temperature for 3 to 4 hours; and (4) cooling the magnesium alloy AZ31 obtained from the step (3) to room temperature. A method for manufacturing a small-peptide-coated biomaterial and an application of the small-peptide-coated biomaterial are further provided.

15 Claims, 8 Drawing Sheets

(51) Int. Cl.
   *B24B 27/033* (2006.01)
   *C22F 1/02* (2006.01)
   *C22F 1/06* (2006.01)
   *B05D 3/00* (2006.01)
   *B05D 7/14* (2006.01)

(52) U.S. Cl.
   CPC ............. *C22F 1/06* (2013.01); *A61L 2430/02* (2013.01); *B05D 3/002* (2013.01); *B05D 7/14* (2013.01)

(56) References Cited

FOREIGN PATENT DOCUMENTS

| | | | |
|---|---|---|---|
| CN | 106715737 | A | 5/2017 |
| CN | 108359919 | A | 8/2018 |
| CN | 109868435 | A * | 6/2019 |
| CN | 109868435 | A | 6/2019 |
| CN | 110042327 | A | 7/2019 |
| CN | 111494704 | A | 8/2020 |
| CN | 111534769 | A | 8/2020 |
| JP | 2011517415 | A | 6/2011 |
| KR | 100768568 | B1 | 10/2007 |
| WO | 2015147184 | A1 | 10/2015 |
| WO | 2016170397 | A1 | 10/2016 |

OTHER PUBLICATIONS

Notice of Reasons for Refusal issued for Japanese Patent Application No. 2022-552864, dated Nov. 14, 2023, 6 pages including English machine translation.

* cited by examiner (a)　　　　　　　　　(b)

A B

C

METHODS FOR IMPROVING MECHANICAL PROPERTY AND BIOLOGICAL STABILITY OF MAGNESIUM ALLOY AND MANUFACTURING MATERIAL AND APPLICATIONS

TECHNICAL FIELD

The present disclosure relates to metal treatment methods and applications, more specifically to methods for improving mechanical property and biological stability of magnesium alloy and manufacturing material and applications.

BACKGROUND

With the development of human society and the increase of human activities, injuries to human bone and hard tissues are becoming more and more frequent, so there is an increasing need for corresponding bone tissue fixation, repair, and replacement biomaterials with higher and higher demand.

Conventional bone fixation and replacement materials (e.g., metal materials such as titanium alloy and stainless steel) would likely cause many problems once implanted into the body due to their great difference with human bone tissue in the mechanical property such as the elasticity modulus: stress shielding, centering infection or inflammatory reaction caused by local pH change resulted from the release of metal ions. As a result, the biocompatibility is poor and it is difficult to adapt to the bone healing process. Polymeric materials are unable to be widely used as bone replacement materials considering their poor mechanical properties, especially their poor plastic, flexible, and radial mechanical properties.

As a typical light alloy, magnesium alloy AZ31 has almost the same elasticity modulus as that of human bone, so its mechanical property is approximate to that of human bone and it is an ideal human bone replacement material. Besides, magnesium is a necessary component of human metabolism and biological reactions. Magnesium has a very good promotion effect on bone growth and strengthening when in combination with osteoblasts. Magnesium has a good biocompatibility as a bone replacement material.

Whereas, since magnesium is very chemically active and various ions are present in human body environment, the magnesium and magnesium alloy AZ31 graft materials have a high degradation rate, resulting in an significant increase in pH value in local body fluid environment, which may trigger alkalosis and then cause local inflammatory reaction, finally causing cell death. Thus, controlling the degradation rate of the magnesium alloy AZ31 in vivo becomes a key issue for the application of the magnesium alloy AZ31 as a bone graft material.

On the other hand, when the magnesium-based alloy is used as the replacement material in vivo and in vitro, since it has no significant antibacterial and anti-inflammatory effects, bacterial overgrowth tends to occur in vivo and in vitro, thereby causing additional inflammatory reaction. This further limits the wide application of the magnesium-based alloy.

In order to solve the problem of too fast degradation of the magnesium-based alloy in vivo, various methods have been used to improve the corrosion resistance of the magnesium. The commonly used methods involve strengthening the surface by various physical and chemical means. Currently, in order to make the materials more bioactive and biocompatible, various coatings with biofunctionality are created. However, the defects of the magnesium-based alloy material itself cause the decreases in the functionality of the surface coating and in the possessed activity, affecting the use of the material. Moreover, the current biofunctional coating can hardly take into account the antibacterial and anti-inflammatory effects while improving the corrosion resistance of the material. Therefore, there is an urgent need to prepare a biofunctional coating which not only can improve the corrosion resistance of the magnesium-based alloy, but also has the anti-inflammatory and antibacterial effects.

SUMMARY

The technical problem to be solved in the present disclosure is to provide a heat treatment method for improving the mechanical property and the biofunctional stability of a magnesium alloy. The magnesium alloy obtained in the method has a good texture structure, has a good binding ability with the corresponding polypeptide, and can maintain a good biofunctionality such as the bacterial inhibition property of the coating.

To solve the above technical problem, the following technological means are adopted in the present disclosure.

A heat treatment method for improving the mechanical property and the biofunctional stability of a magnesium alloy, including steps of:

(1) fully annealing an original cold-drawn magnesium alloy AZ31 in an interference-free atmosphere which eliminates the original processing stress and the texture structure specificity of the cold-drawn magnesium alloy AZ31;

(2) polishing a surface of the magnesium alloy AZ31 from the step (1) by a waterproof abrasive paper to remove an original oxide layer on the surface while maintaining or improving the finish of the surface;

(3) heating the magnesium alloy AZ31 obtained from the step (2) in an interference-free atmosphere created by an inert gas or a vacuum, wherein the magnesium alloy AZ31 is heated to a temperature of 330° C. to 350° C. in the interference-free atmosphere and then the temperature is kept for 3 to 4 hours to fully anneal the magnesium alloy AZ31 obtained from the step (2);

(4) letting the magnesium alloy AZ31 obtained from the step (3) complete its fully annealing in the interference-free atmosphere, by cooling the magnesium alloy AZ31 obtained from the step (3) along with a furnace to room temperature, to obtain an equiaxed crystal structure which is texture-even and isotropic.

The magnesium alloy AZ31 manufactured by the present method has a good texture structure, with a grain size of about 16 μm. It is demonstrated that the hardness is about 73 HV. The magnesium alloy AZ31 has a good binding ability with the corresponding polypeptide, and can maintain a good biofunctionality such as the bacterial inhibition property of the coating.

Further, the preferred technical solutions are as follows.

The polishing the surface of the magnesium alloy AZ31 by the waterproof abrasive paper includes initial polishing and finishing. The initial polishing is performed with a 400-mesh waterproof abrasive paper for 1 to 3 minutes to remove the original oxide layer, and then the finishing is immediately performed, wherein the finishing is performed with a 1200-mesh to 2400-mesh waterproof abrasive paper for 2 to 5 minutes, to keep the surface finish of the magnesium alloy AZ31.

The above polishing manner is helpful to remove the oxide layer on the surface of the magnesium alloy AZ31, and makes the surface clean and having a high finish.

The initial polishing includes grinding along one direction, with the strength effective to remove the oxide layer. The initial polishing is performed until the dark oxide layer on the surface of the magnesium alloy AZ31 is fully removed to expose the silver white magnesium metal itself. The grinding direction in the finishing process is perpendicular to the direction of the initial polishing, with the strength smaller than that in the initial polishing, until there is no obvious scratch on the surface of the magnesium alloy AZ31.

The above polishing manner is helpful to remove the oxide layer on the surface of the magnesium alloy AZ31, and makes the surface clean and having a high finish.

Another technical problem to be solved in the present disclosure is to provide a method for manufacturing a small-peptide-coated magnesium alloy biomaterial and the application of the small-peptide-coated magnesium alloy biomaterial. The magnesium alloy biomaterial manufactured by this method has a biofunctional coating which is anti-inflammatory and antibacterial. The corrosion resistance of the magnesium alloy can also be improved. The magnesium alloy biomaterial has good biological activity and human body compatibility, and can be applied in the manufacture of a hard-tissue defect repair material.

To solve the above technical problem, the following technological means are adopted in the present disclosure.

A method for manufacturing a small-peptide-coated magnesium-based alloy biomaterial includes: ultrasonically cleaning a magnesium-based alloy AZ31 to remove impurities on a surface of the magnesium-based alloy AZ31; dissolving polyurethane with chloroform, and then placing the treated magnesium-based alloy AZ31 into the chloroform solution dissolved with the polyurethane in a plasma reactor, so that the magnesium-based alloy AZ31 is fully enclosed by the solution; taking out the magnesium-based alloy AZ31, and letting the magnesium-based alloy AZ31 stand until the solution on the surface thereof is solidified, and then activating the polyurethane coated on the surface of the magnesium-based alloy AZ31 by using a click reaction in the plasma reactor; and finally placing the surface-activated polyurethane-coated magnesium-based alloy AZ31 into a sodium phosphate solution dissolved with polypeptide and applying vibration to allow them fully react to form the corresponding polypeptide coating.

The stable biological coating is formed in the magnesium-based alloy biomaterial in the present disclosure, improving the bacterial inhibition property and the corrosion resistance of the magnesium alloy.

Further, the preferred technical solutions are as follows.

The magnesium-based alloy AZ31 is the cold-drawn magnesium-based alloy AZ31 or the magnesium-based alloy AZ31 fully annealed in the interference-free atmosphere.

In the ultrasonic cleaning, the cleaning is performed for 3 to 5 minutes, and the cleaning liquid is pure water or 80% ethyl alcohol, in order to remove the impurities on the surface of the magnesium-based alloy AZ31 and keep the surface of the magnesium-based alloy AZ31 clean.

The chloroform solution of polyurethane is a uniform, colourless, transparent, and viscous solution formed by mixing the white solid polyurethane with colourless and transparent chloroform solution having the purity not less than 99.5% in a ratio of 3 g:100 ml and then being vibrated and stirred at normal temperature.

The magnesium-based alloy AZ31 is placed into the chloroform solution of polyurethane, fully immersed for 60 minutes, and intermittently vibrated and stirred.

In the solidification of the solution on the surface of the magnesium-based alloy AZ31, chloroform is quickly volatilized so that one uniform, dense, and stable polyurethane coating is formed on the metal surface.

The magnesium-based alloy AZ31 with the solution on its surface solidified is surface-treated with oxygen plasma at 2.45 GHz for 1 minute in the plasma reactor and then stands in the atmospheric environment for 15 minutes to further promote the formation of peroxide groups and hydroxyl groups on the surface.

The magnesium-based alloy AZ31 is moved back into the plasma reactor after it is subjected to the further promoting the formation of peroxide groups and hydroxyl groups on the surface. The vacuum degree is adjusted to 26.7. Acrylic acid vapor is slowly introduced until reaching 66.7 Pa. After reacting for 1 minute, the magnesium-based alloy AZ31 is taken out and cleaned for 10 minutes in an ultrasonic cleaner. Thereafter, the magnesium-based alloy AZ31 is transferred into a mixed aqueous solution, with pH of 5.0, of 1.25 mg/ml N-hydroxysuccinimide and 5 mg/ml 1-ethyl-3-(3-dimethylaminopropyl) carbodiimide, vibrated and stirred for 20 hours at 4° C., and then taken out. Finally, the polyurethane coated on the surface of the magnesium-based alloy AZ31 is activated.

The sodium phosphate solution of polypeptide is a 5 mM uniform solution prepared by dissolving the polypeptide F3 with the purity greater than 95% into 0.1 M sodium phosphate solution.

The magnesium-based alloy AZ31 is enclosed by the sodium phosphate solution containing the polypeptide, taken out after 20 hours of vibration, ultrasonically cleaned in ultrapure water for 10 minutes for twice, and dried, so that the manufacture is completed.

The small-peptide coated magnesium-based alloy biomaterial has good biological activity and human body compatibility, and can be applied in the manufacture of a hard-tissue defect repair material.

The small-peptide coated magnesium-based alloy biomaterial can be applied in the manufacture of a bone fixation material.

Based on its good biological activity and human body compatibility, the small-peptide coated magnesium-based alloy biomaterial can be widely used in artificial prosthesis, implantable replacement material repair of open trauma of human tissue, intraoral dental implant, repair of damage of tissue in body, and manufacture of human biomaterial such as biological catheter, joint bowl, and tubular joint nail.

BRIEF DESCRIPTION OF THE DRAWINGS

FIG. 4 is a comparison of bacteria inhibition effects of the annealed magnesium alloy AZ31 and the original cold-drawn magnesium alloy AZ31 after combination with the small-molecule polypeptides, wherein FIG. 4A is a picture after 24 hours of bacteria inhibition reaction of the sample of the magnesium alloy AZ31 in the present disclosure chelated with the small-molecule peptide F3, FIG. 4B is a picture after 48 hours of bacteria inhibition reaction of the sample of the magnesium alloy AZ31 in the present disclosure chelated with the small-molecule peptide F3, FIG. 4C is a picture after 24 hours of bacteria inhibition reaction of the sample of the original cold-drawn AZ31 chelated with the small-molecule peptide F3, and FIG. 4D is a picture after 48 hours of bacteria inhibition reaction of the sample of the original cold-drawn AZ31 chelated with the small-molecule peptide F3.

DETAILED DESCRIPTION

Example 1

Referring to FIGS. 1 to 4, a heat treatment method for improving the mechanical property and the biofunctional stability of a magnesium alloy, including steps of:

(1) fully annealing an original cold-drawn magnesium alloy AZ31 in an interference-free atmosphere which eliminates the original processing stress and the texture structure specificity of the cold-drawn magnesium alloy AZ31;

(2) polishing a surface of the magnesium alloy AZ31 from the step (1) by a waterproof abrasive paper to remove an original oxide layer on the surface while maintaining or improving the finish of the surface; the polishing the surface of the magnesium alloy AZ31 by the waterproof abrasive paper includes initial polishing and finishing; the initial polishing is performed with a 400-mesh waterproof abrasive paper for 1 to 3 minutes to remove the original oxide layer, and then the finishing is immediately performed, wherein the finishing is performed with a 1200-mesh to 2400-mesh waterproof abrasive paper for 2 to 5 minutes, to keep the surface finish of the magnesium alloy AZ31; the initial polishing includes grinding along one direction, with the strength effective to remove the oxide layer; the initial polishing is performed until the dark oxide layer on the surface of the magnesium alloy AZ31 is fully removed to expose the silver white magnesium metal itself; the grinding direction in the finishing process is perpendicular to the direction of the initial polishing, with the strength smaller than that in the initial polishing, until there is no obvious scratch on the surface of the magnesium alloy AZ31.

Figure 1:
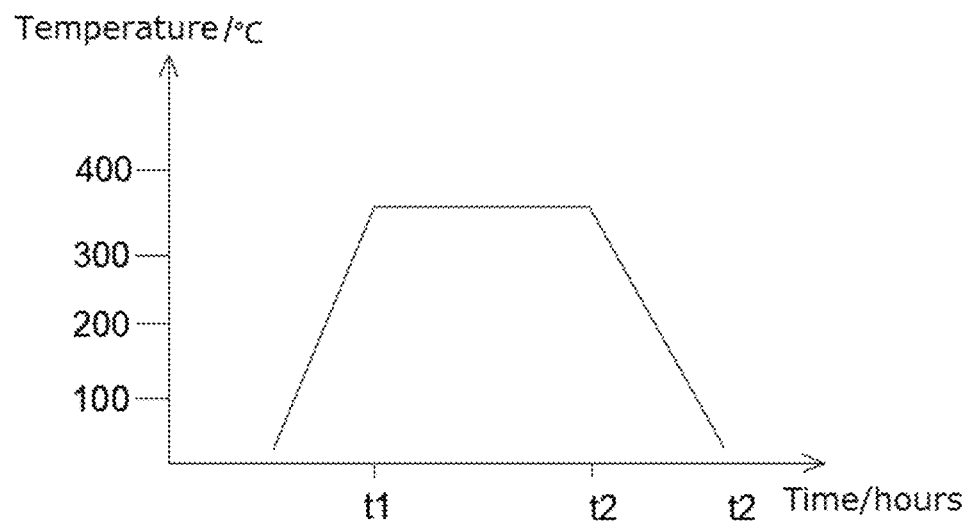
FIG. 1 is a schematic view of fully annealing a material in an interference-free atmosphere.
Figure 2:
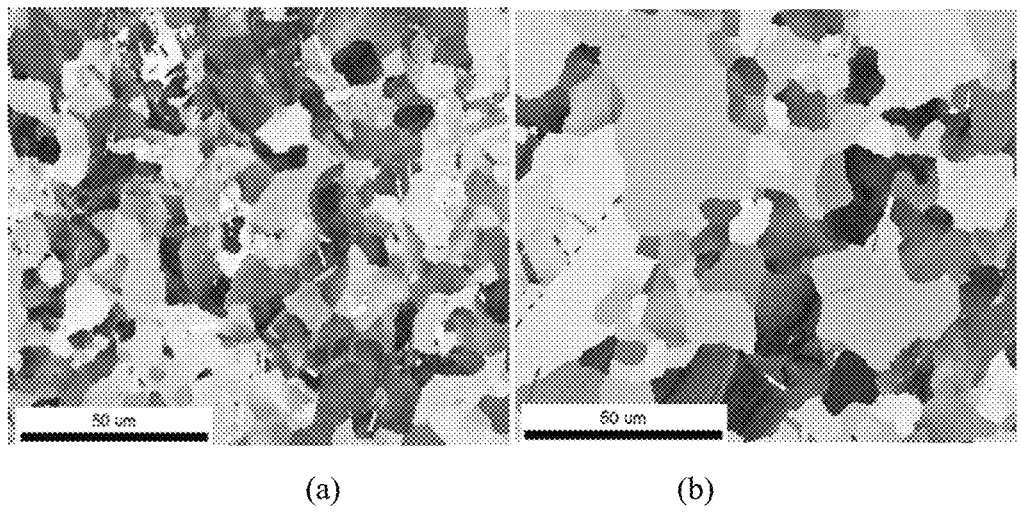
FIG. 2 is a comparison of textures of annealed magnesium alloy AZ31 and original cold-drawn magnesium alloy AZ31, wherein (a) shows the texture structure of the cold-drawn magnesium alloy AZ31 which has not been treated, and (b) shows the texture structure of the magnesium alloy AZ31 fully annealed in the interference-free atmosphere.
Figure 3:
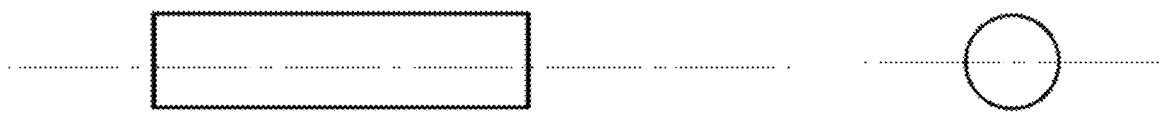
FIG. 3 is a schematic structural view of a bone nail manufactured from the magnesium alloy.
Figure 4:
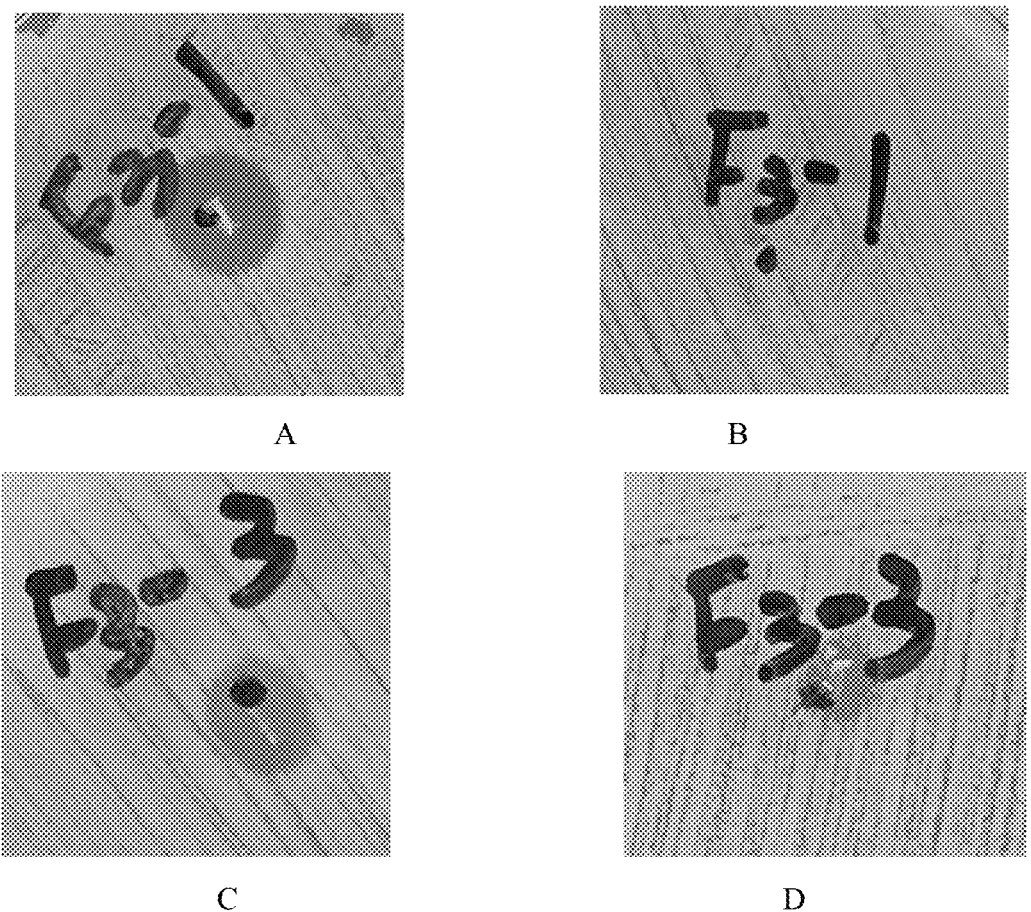
Figure 5:
FIG. 5 is a schematic structural view of a sample manufactured from the magnesium alloy for the in-vitro corrosion experiment.
Figure 6:
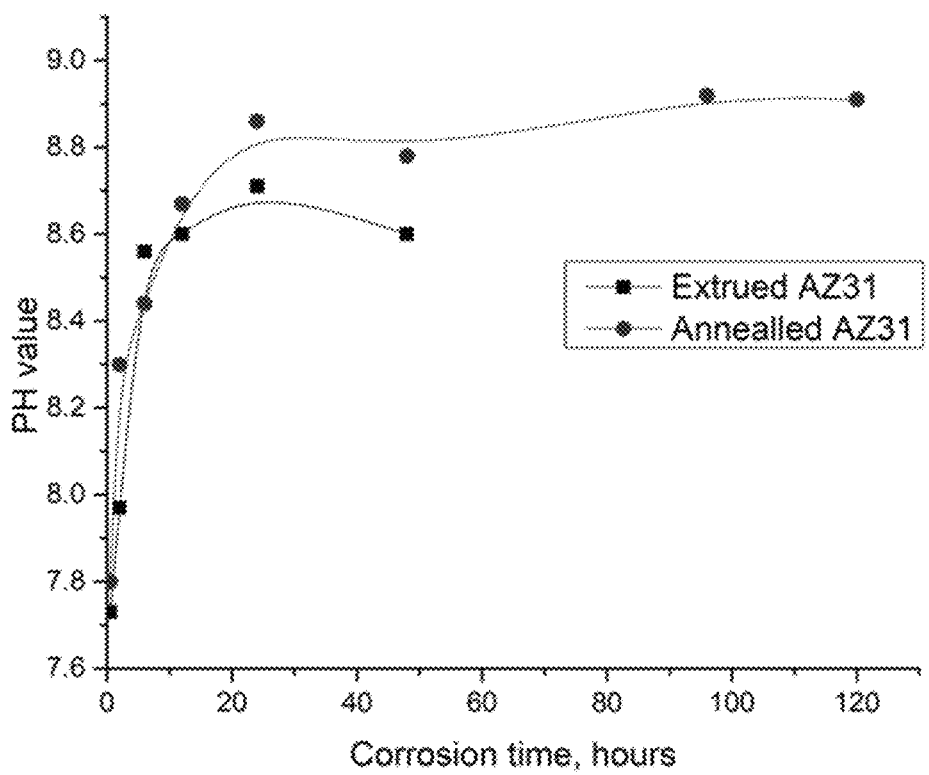
FIG. 6 shows the changes in pH values after 5 days of in-vitro corrosion experiments conducted with samples of annealed AZ31 magnesium alloy and cold-extruded magnesium alloy as well as pure magnesium alloy.
Figure 7:
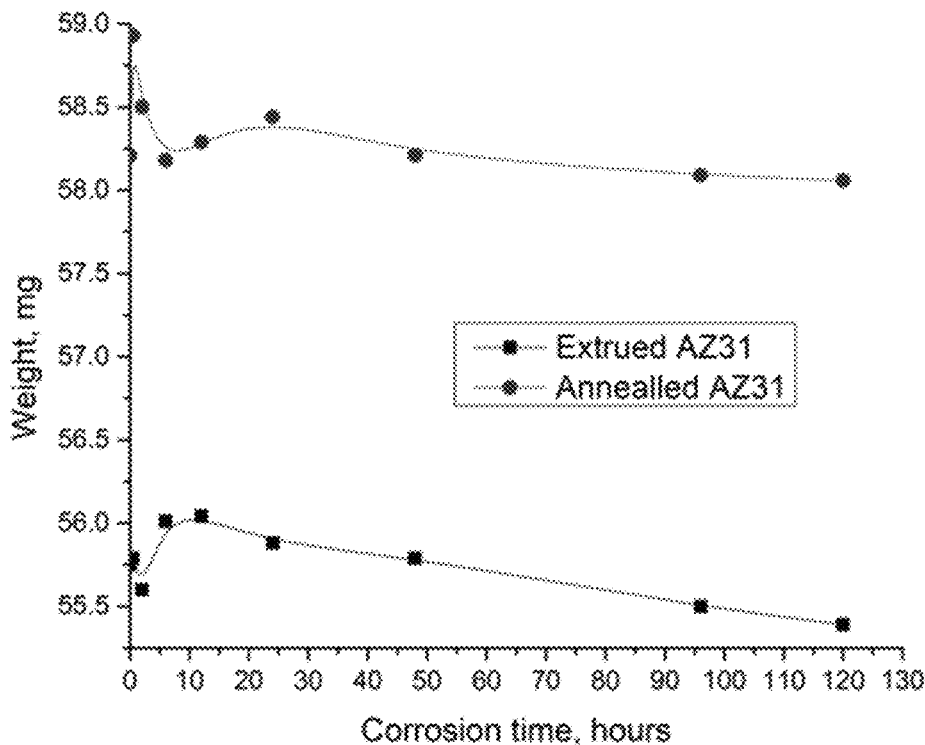
FIG. 7 shows the changes in weights of samples after 5 days of in-vitro corrosion experiments conducted with samples of annealed AZ31 magnesium alloy and cold-extruded magnesium alloy as well as pure magnesium alloy.
Figure 8:
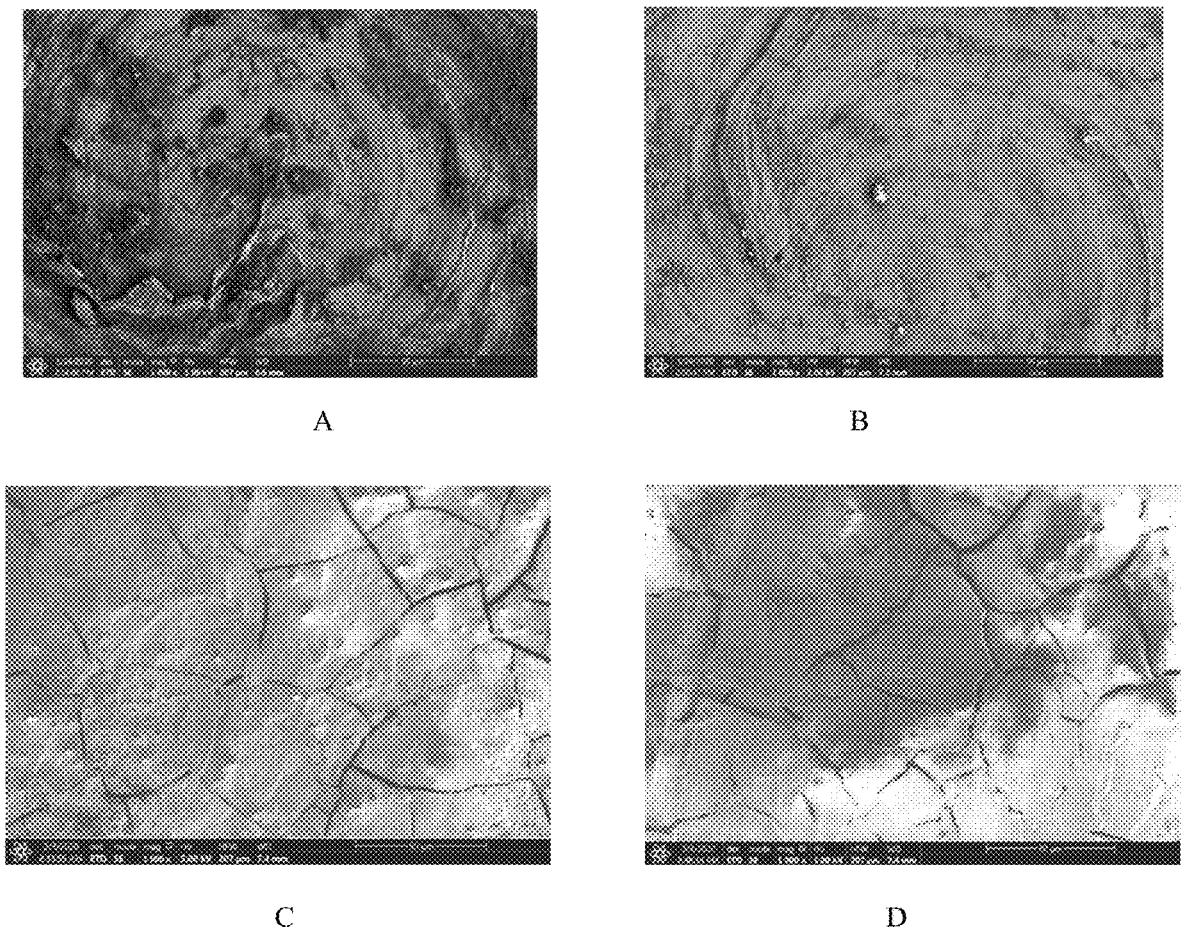
FIG. 8 shows the surface morphologies of samples after 5 days of in-vitro corrosion experiments, wherein A: the surface morphology of the cold-drawn AZ31 sample before the in-vitro corrosion, B: the surface morphology of the annealed AZ31 sample before the in-vitro corrosion, C: the surface morphology of the cold-drawn AZ31 sample after 120 hours of the in-vitro corrosion, D: the surface morphology of the annealed AZ31 sample after 120 hours of the in-vitro corrosion.

(3) heating the magnesium alloy AZ31 obtained from the step (2) in an interference-free atmosphere created by an inert gas or a vacuum, wherein the magnesium alloy AZ31 is heated to a temperature of 330° C. to 350° C. in the interference-free atmosphere and then the temperature is kept for 3 to 5 hours which is corresponding to the time from t1 to t2 in FIG. 1 to fully anneal the magnesium alloy AZ31 obtained from the step (2);

(4) letting the magnesium alloy AZ31 obtained from the step (3) complete its fully annealing in the interference-free atmosphere, by cooling the magnesium alloy AZ31 obtained from the step (3) along with a furnace to room temperature, to obtain an equiaxed crystal structure which is texture-even and isotropic.

The texture structures of the AZ31 before and after the heat treatment are compared by observing metallographic structures via the field emission scanning microscopy. The annealed AZ31 magnesium alloy AZ31 has a grain size of 15.8 μm, while the original cold-drawn magnesium alloy AZ31 has a grain size of 9.2 μm. The hardness of the AZ31 is measured by Vickers micro hardness tester, and the change in Vickers hardness before and after the heat treatment is compared. The untreated AZ31 has a Vickers hardness of 83.9 HV, while the AZ31 fully annealed in the interference-free atmosphere has a Vickers hardness of 72.8 HV.

(1) Bacterial Inhibition Comparison Experiment (1) The original cold-drawn magnesium alloy AZ31 and the AZ31 obtained by the present method are made into small-sized bone nails which have a diameter of 0.5 mm and a length of 2 mm, with a size tolerance of ±0.005 mm;

(2) The two kinds of small-sized bone nails processed from two kinds of alloys are combined with small-molecule polypeptide F3 via a chelation reaction, so that one coating of small peptide F3 is formed on a surface of each of bone nails;

(3) The samples of two kinds of magnesium alloys AZ31 after the chelation reaction are subjected to 48 hours of bacterial inhibition experiments conducted with the drug-resistant *Staphylococcus aureus* to observe the bacterial inhibition properties of the two materials. The results thereof are listed in the following table.

TABLE 1

Comparison of bacterial inhibition effects

| | diameter of bacterial inhibition zone (mm) | |
|---|---|---|
| Material | 24 hours | 48 hours |
| original cold-drawn AZ31 bone nail chelated with small peptide F3 | 7.32 | 0 |
| interference-free atmosphere fully annealed AZ31 bone nail chelated with small peptide F3 | 5.38 | 3.8 |

(4) Experiment conclusion based on analysis: by comparing the experiment results, it can be seen that as compared to cold-drawn magnesium alloy AZ31 chelated with small peptide F3, the magnesium alloy AZ31 fully annealed in the interference-free atmosphere and chelated with polypeptide F3 has more stable and more durable bacterial inhibition property: the excellent bacterial inhibition property on the drug-resistant *Staphylococcus aureus* can be maintained for 48 hours; while the cold-drawn AZ31 chelated with polypeptide F3 fully lost the bacterial inhibition effect on the drug-resistant *Staphylococcus aureus* after 48 hours.

(II) In-Vitro Corrosion Comparison Experiment (1) The original cold-drawn magnesium alloy AZ31 and the AZ31 obtained by the present method are made into small-sized magnesium sheets which have a diameter of 4.4 mm and a thickness of 2 mm, with a size tolerance of ±0.002 mm;

(2) The two metal samples are placed into high glucose mediums DMEM (Dulbecco's Modified Eagle Medium) and subjected to in-vitro corrosion-resistance experiments in an incubator at 37° C. for 120 hours;

(3) In the process of in-vitro corrosion, the weights of the samples and the pH values of the DMEM mediums are detected periodically. The specific observation items and steps and the observation results are as follows.

TABLE 2

Comparison of results of in-vitro corrosion experiments

| | pH value/sample weight (mg) | | | | | | | | |
|---|---|---|---|---|---|---|---|---|---|
| material | intial | 30 mins | 2 h | 6 h | 12 h | 24 h | 48 h | 96 h | 120 h |
| original cold-drawn AZ31 magnesium sheet sample | 7.2/ 55.75 | 7.73/ 55.79 | 7.97/ 55.6 | 8.56/ 56.01 | 8.6/ 56.04 | 8.71/ 55.88 | 8.6/ 55.79 | —/ 55.5 | —/ 55.39 |
| interference-free atmosphere fully annealed AZ31 magnesium sheet sample | 7.2/ 58.21 | 7.8/ 58.93 | 8.3/ 58.5 | 8.44/ 58.18 | 8.67/ 58.29 | 8.86/ 58.44 | 8.78/ 58.21 | 8.92/ 58.09 | 8.91/ 58.06 |

(4) after the in-vitro corrosion experiment is completed, SEM is used to observe the morphologies of the surfaces of the two samples.

(5) Experiment conclusion based on analysis: by comparing the experiment results, it can be seen that as compared to the cold-drawn magnesium alloy AZ31, the sample of the magnesium alloy AZ31 fully annealed in the interference-free atmosphere has more stable and more durable corrosion resistance: it can be remained for 120 hours in the DMEM; while for the cold-drawn AZ31, after 48 hours, the corrosion is speed up, and the weight loss of the sample is accelerated, suggesting that there is totally no resistance to corrosion from DMEM. From the observation of the surface morphologies, after 120 hours of corrosion, a large amount of obvious layered or squamous exfoliations is formed on the surface of the cold-drawn magnesium alloy AZ31, suggesting obvious surface corrosion; while there is no obvious layered or squamous exfoliation on the surface of the AZ31 fully annealed in the interference-free atmosphere, and the surface is kept relatively integral.

In the method in this Example 1, the process is simple, the operation is convenient, the implementability is high, the new material formed is stable, and can be combined with other material to form a stable structure; the activity of the combined product can be maintained and enhanced; the energy consumption is small, it is easy to produce with short period and easy to be industrialized, and there is no pollution for environment.

Example 2

The present disclosure will be further described in the below with reference to Example 2.

Figure 9:
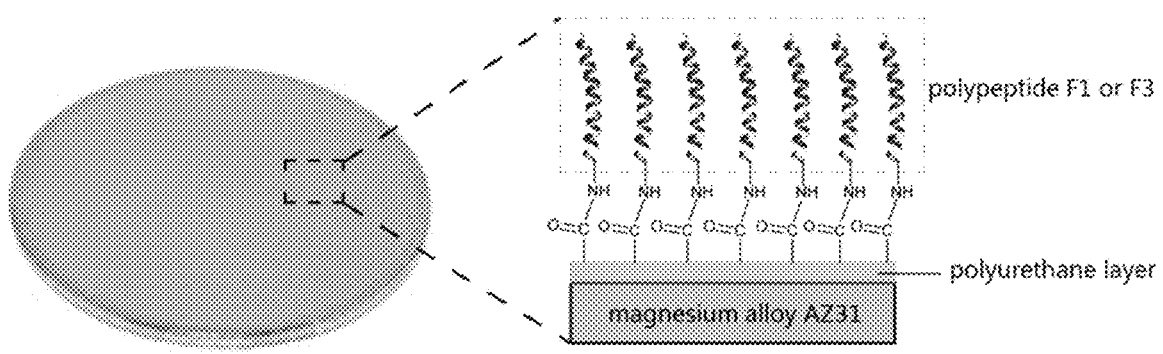
FIG. 9 is a schematic view of the combination of magnesium alloy with polyurethane and polypeptide.

This example provides a method for manufacturing a polypeptide bio-coating, which can improve the bacterial inhibition property and the corrosion resistance property of the magnesium alloy, via a chemical click reaction (see FIG. 9), including the following steps.

The cold-drawn magnesium alloy AZ31 and the magnesium alloy AZ31 fully annealed in the interference-free atmosphere are processed into sheet pieces which have a diameter of 4.4 mm and a thickness of 2 mm.

The surfaces of the two magnesium alloy samples processed into sheet shapes are cleaned, wherein the cleaning is performed for 3 to 5 minutes by using ultrasonic wave, and the cleaning liquid is pure water (alternatively, 80% ethyl alcohol), to remove the impurities and adhesions on the surfaces, so that the surfaces of the two samples are kept clean.

The polyurethane produced from Selectophore™ (class MQ100) is selected as a coating agent of the metal surface.

First, the white solid polyurethane particles and the colourless and transparent chloroform solution (with the purity≥99.5%) are mixed in a ratio of 3 g:100 ml (W/V) and then vibrated and stirred at normal temperature until the polyurethane is fully dissolved and a uniform, colourless, transparent, and viscous solution is formed.

The two magnesium-based alloys AZ31 (in sheet shape, with diameter of 4.4 mm and thickness of 2 mm) which have been surface-treated by ultrasonic wave are placed into the chloroform solution of polyurethane, fully immersed for 60 minutes, and intermittently vibrated and stirred.

The two magnesium alloy materials with the polyurethane uniformed coated thereon are taken out from the solution, placed into watch-glass, and then put in the fume cupboard for 16 hours to allow chloroform to be quickly volatilized so that one uniform, dense, and stable polyurethane coating is formed on the metal surface.

The coated metal sheets are placed into a plasma reactor (manufactured by MiniFlecto®, Plasma Technology GmbH) and surface-treated with oxygen plasma at 2.45 GHz for 1 minute, and then stand in the atmospheric environment for 15 minutes to further promote the formation of peroxide groups and hydroxyl groups on the surface.

The metals are moved back into the plasma reactor. The vacuum degree is adjusted to 26.7. Acrylic acid vapor is slowly introduced until reaching 66.7 Pa. After reacting for 1 minute, the metals are taken out and cleaned for 10 minutes in an ultrasonic cleaner. Thereafter, the metals are transferred into a mixed aqueous solution (with pH of 5.0) of 1.25 mg/ml N-hydroxysuccinimide and 5 mg/ml 1-ethyl-3-(3-dimethylaminopropyl) carbodiimide, vibrated and stirred for 20 hours at 4° C., and then taken out. Finally, the polyurethanes coated on the surfaces of the magnesium-based alloys AZ31 are activated.

The synthetic high purity (>95%) polypolypeptides F1 and F3 (which were found in the gland at the back of the Australian tree frog) are separately dissolved into 0.1 M sodium phosphate solution to prepare an 5 mM uniform solution. The surface-activated polyurethane-coated metal sheets are immersed into the sodium phosphate solution of polypeptide at 4° C., taken out after 20 hours of vibration, ultrasonically cleaned for 10 minutes in ultrapure water for twice, and dried in the fume cupboard, so that the maufacture is completed.

(I) Bacterial Inhibition Comparison Experiment (1) The samples for the bacterial inhibition experiment are all made into small-sized magnesium sheets which have a diameter of 4.4 mm and a thickness of 2 mm, with a size tolerance of ±0.002 mm;

(2) The original magnesium alloys AZ31 in two different treatment states and the two magnesium alloy samples respectively formed with F1 and F3 polypeptide coatings via the click reaction are subjected to the surface-cleaning: the cleaning is performed with pure water, the cleaning is performed in the ultrasonic cleaner for 3 to 5 minutes to remove the impurities and the adhesions on the surfaces;

(3) The cleaned samples are placed into bacterial inhibition experiment vessels and subjected to 100 hours of bacterial inhibition experiments in 37° C. incubator conducted with the drug-resistant *Staphylococcus aureus*.

Figure 10:
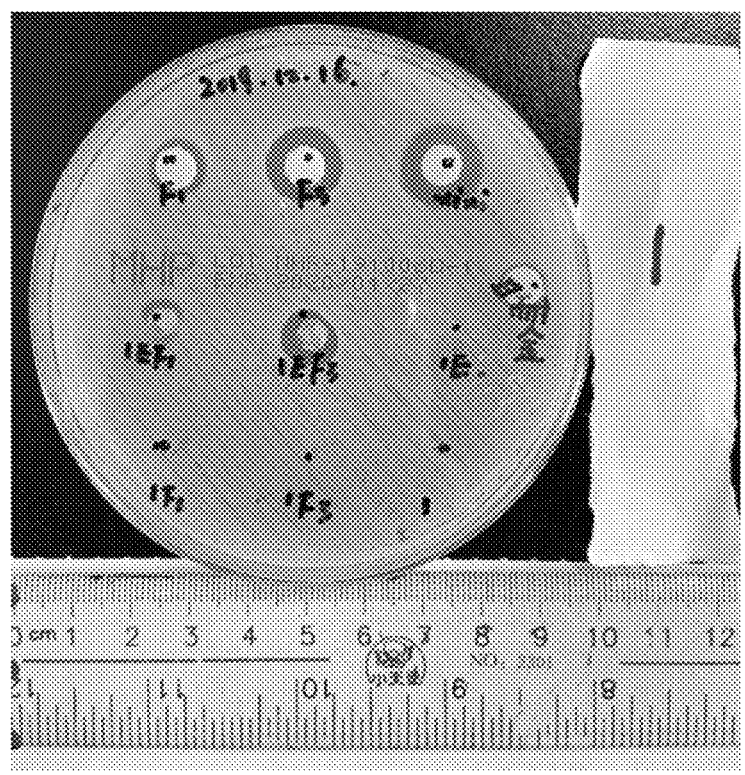
FIG. 10 is a picture of experiments with drug-resistant *Staphylococcus aureus*.

(4) The methicillin-resistant *Staphylococcus aureus* (MRSA, GDM1.1263) grown in the logarithmic phase are collected. MH mediums are adjusted to bacterial suspensions with the concentration of $2.0 \times 10^5$ CFU/ml. Sterile cotton swabs are dipped into the bacterial suspensions, and the tube walls are rotated and squeezed several times to remove excess bacterial suspensions. The whole M-H drug-sensitive agar plates (Guangzhou Yuanming Bio) are uniformly swabbed by the swabs. Drug-sensitive paper disks (OXOID, UK) are respectively added with 30 μg of F1 and F3 polypeptides. The paper disks are attached onto the M-H agar plates. The plates are placed upside down, and incubated at 37° C. overnight. 30 μg of Tazocin (piperacillin sodium and tazobactam sodium) and blank drug-sensitive disk (BASD) and the original AZ31 magnesium alloys in two states are used as controls. The pictures of the bacterial inhibition experiments are shown in FIG. 10. The sizes of the bacterial inhibition zones are measured with a vernier caliper. The results are shown in the following table.

TABLE 3

Bacterial inhibition effect comparison

| sample | Diameter of bacterial inhibition zone (mm) | | | | |
|---|---|---|---|---|---|
| | 0 h | 24 h | 48 h | 72 h | 100 h |
| F1 | 7.47 | 9.24 | 7.47 | 7.47 | 7.47 |
| F3 | 7.47 | 12.4 | 7.47 | 7.47 | 7.47 |
| blank drug-sensitive disk (white) | 7.47 | 7.47 | 7.47 | 7.47 | 7.47 |
| 30 μg Tazocin + blank drug-sensitive disk (Xini) | 7.47 | 12.72 | 7.47 | 7.47 | 7.47 |
| Cold-drawn AZ31 (1E) | 4.4 | 4.4 | 4.4 | 4.4 | 4.4 |
| Cold-drawn AZ31 coated with F1 coating (1EF1) | 4.4 | 6.1 | 4.4 | 4.4 | 4.4 |
| Cold-drawn AZ31 coated with F3 coating (1EF3) | 4.4 | 9.83 | 7.73 | 6.88 | 5.05 |
| Annealed AZ31 (3A) | 4.4 | 4.4 | 4.4 | 4.4 | 4.4 |
| Annealed AZ31 coated with F1 coating (3AF1) | 4.4 | 7.39 | 4.4 | 4.4 | 4.4 |
| Annealed AZ31 coated with F3 coating (3AF3) | 4.4 | 11.91 | 7.82 | 7.03 | 6.08 |

Note:
Tazocin includes piperacillin sodium and tazobactam sodium with a mass ratio of 8:1

Figure 11:
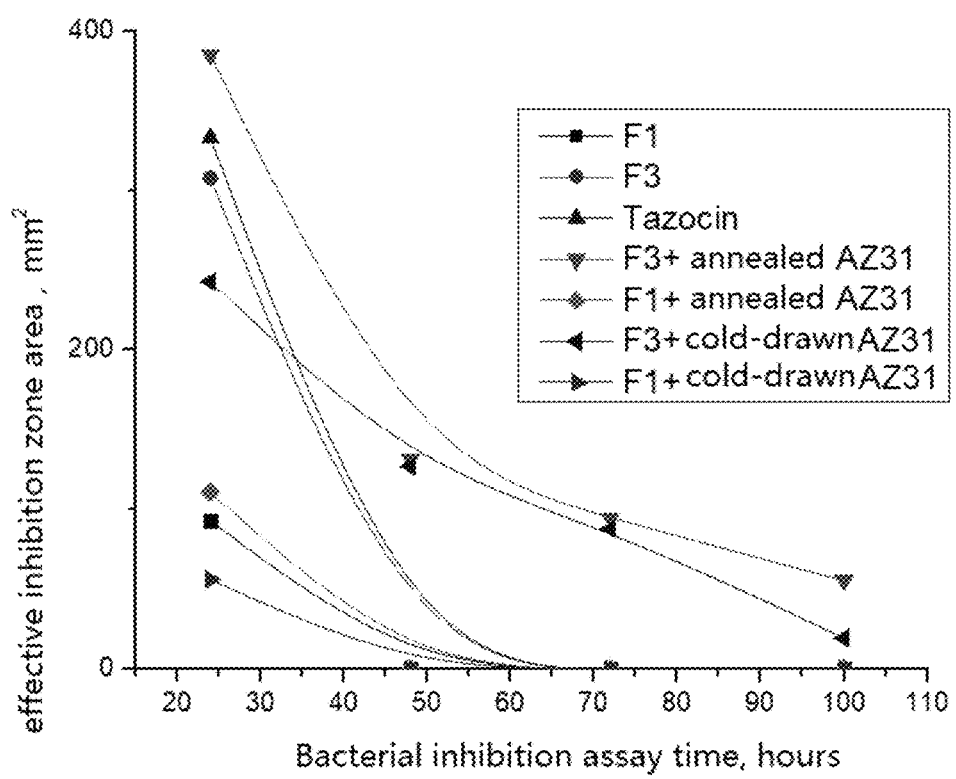
FIG. 11 is a comparison of results and analysises of bacterial inhibition experiments.

(4) Experiment conclusion based on analysis: by comparing the experiment results, it can be seen that:

(i) The two pure metal samples (cold-drawn AZ31 and annealed AZ31) both have no bacterial inhibition effect;

(ii) The blank drug-sensitive disk has no bacterial inhibition effect;

(iii) The existing clinical drug Tazocin has best bacterial inhibition effect within 24 hours and the bacterial inhibition effect disappears after 24 hours;

(iv) both of the pure polypeptide F1 and the pure polypeptide F3 have obvious bacterial inhibition effect within 24 hours, however, similar to the Tazocin, the bacterial inhibition effect disappears after 24 hours; the bacterial inhibition effect of the polypeptide F3 is significantly better than the polypeptide F1;

(v) Both of the samples of two magnesium alloys AZ31 coated with the polypeptide F1 coatings exhibit obvious bacterial inhibition effect within 24 hours, however, the bacterial inhibition effect disappears after 24 hours; the bacterial inhibition effect of the annealed AZ31 coated with the polypeptide F1 coating is significantly better than the bacterial inhibition effect of cold-drawn AZ31 coated with the polypeptide F1 coating;

(vi) Both of the samples of the two magnesium alloys AZ31 coated with the polypeptide F3 coatings exhibit obvious and durable bacterial inhibition effects within 100 hours. However, there are trends of progressive decrease in the bacterial inhibition effects. Moreover, the bacterial inhibition effect of the annealed AZ31 coated with the polypeptide F3 coating is significantly better than the bacterial inhibition effect of cold-drawn AZ31 coated with the polypeptide F3 coating;

(vii) Since the magnesium alloy coated with the polypeptide coating has a diameter greatly different from that of the drug-sensitive disk swabbed with the Tazocin, its bacterial inhibition effect cannot be directly compared with Tazocin; thus, the comparison is made on the effective areas of bacterial inhibition zones. As shown in FIG. 11, the bacterial inhibition effect of the sample of annealed AZ31 coated with the polypeptide F3 coating at 24 hours is significantly higher than the existing clinical drug Tazocin, and is still significant even after 100 hours. Besides, the cold-drawn AZ31 metal sheet coated with F3 exhibits durable and outstanding bacterial inhibition effect for 100 hours.

(II) Comparison of Results of In-Vitro Corrosion-Resistance Experiments (1) The samples to be corroded (the original magnesium alloys AZ31 in two different treatment states and the two magnesium alloys respectively coated with F1 and F3) are all made into small-sized magnesium sheets which have a diameter of 4.4 mm and a thickness of 2 mm, with a size tolerance of ±0.002 mm;

(2) The original magnesium alloys AZ31 in two different treatment states and the samples of two magnesium alloys respectively formed with polypeptide F1 and F3 coatings via the click reaction are subjected to the surface-cleaning: the cleaning is performed with pure water, the cleaning is performed in the ultrasonic cleaner for 3 to 5 minutes to remove the impurities and the adhesions on the surfaces;

(3) The prepared samples to be corroded are respectively placed into high glucose mediums DMEM (Dulbecco's Modified Eagle Medium) and subjected to the in-vitro corrosion-resistance experiments in an incubator at 37° C. for 120 hours;

(4) In the process of in-vitro corrosion, the weights of the samples and the pH values of the DMEM mediums are detected periodically. The specific observation items and steps are as follows:

(i) after a period of corrosion, the samples are taken out, washed, and then dried in the bio-safety fume cupboard. Thereafter, the weighs are measured with the electronic balance (Japan Shimadzu electronic balance AUW22D).

(ii) after the step (1), the pH values of the DEEM mediums with the samples taken out therefrom are measured with the pH detector (CyberScan pH510-desk type pH acidometer).

The experiment results are shown in Table 4

TABLE 4

| Comparison of results of in-vitro corrosion experiments | | | | | | | | | |
|---|---|---|---|---|---|---|---|---|---|
| | weight(mg)/pH(DM EM) | | | | | | | | |
| material | intial | 30 mins | 2 h | 6 h | 12 h | 24 h | 48 h | 96 h | 120 h |
| cold-drawn AZ31 magnesium sheet sample (IE) | 55.75/ 7.2 | 55.79/ 7.73 | 55.60/ 7.97 | 56.01/ 8.56 | 56.04/ 8.60 | 55.88/ 8.71 | 55.79/ 8.6 | 55.46/ 7.16 * | 55.40/ 7.15 * |
| cold-drawn AZ31 magnesium sheet coated with F1 coating (1EF1) | 55.38/ 7.2 | 56.12/ 7.66 | 54.8/ 8.03 | 54.94/ 8.38 | 54.87/ 8.50 | 54.65/ 6.5 * | 54.70/ 7.88 * | 54.75/ 7.31 * | 54.74/ 7.77 * |
| cold-drawn AZ31 magnesium sheet coated with F3 coating (1EF3) | 54.36/ 7.2 | 54.38/ 7.64 | 53.90/ 8.05 | 54.43/ 8.31 | 54.48/ 8.49 | 54.41/ 8.54 | 54.36/ 8.47 | 54.23/ 6.78 * | 54.21/ 7.95 * |
| annealed AZ31 magnesium sheet (3A) | 58.21/ 7.2 | 58.93/ 7.80 | 58.50/ 8.30 | 58.18/ 8.44 | 58.29/ 8.67 | 58.44/ 8.86 | 58.21/ 8.78 | 58.09/ 8.92 | 58.06/ 8.91 |
| annealed AZ31 magnesium sheet coated with F1 coating (3AF1) | 56.59/ 7.2 | 56.40/ 7.63 | 55.70/ 8.17 | 55.84/ 8.28 | 56.00/ 8.53 | 56.00/ 8.54 | 56.00/ 8.50 | 56.06/ 8.42 | 55.71/ 6.78 * |
| annealed AZ31 magnesium sheet coated with F3 coating (3AF3) | 59.37/ 7.2 | 58.66/ 7.64 | 58.20/ 8.11 | 58.08/ 8.29 | 58.26/ 8.40 | 58.31/ 8.5 | 58.23/ 8.46 | 58.38/ 8.66 | 58.29/ 8.31 |

Note:
* represents that the solution with the corresponding pH value is slightly polluted by bacteria With reference to Table 4 showing the experiment results, the observation results for specific pH values are as follows.

Figure 14:
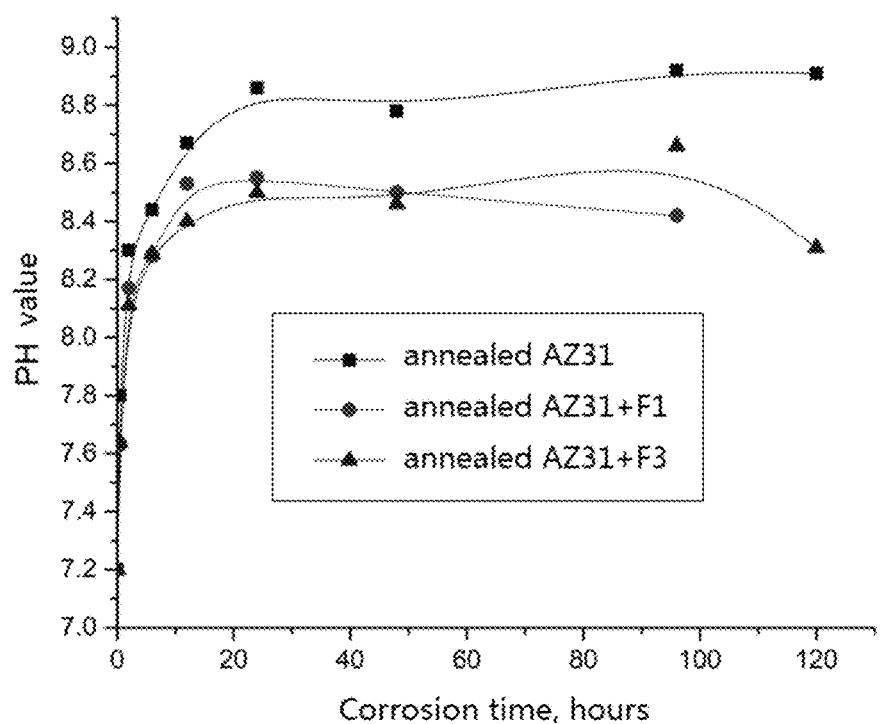
FIG. 14 shows the change analysises of pH values in the in-vitro corrosion experiments.

As shown in FIG. 14, in the process of 120 hours of in-vitro corrosion, taken a set of samples of annealed AZ31 as example, in the process of 120 hours of in-vitro corrosion of pure metal AZ31, the pH value of the DMEM solution corresponding thereto is surged from an initial value of 7.2 to 8.91. Moreover, in the whole corrosion process, its pH value is highest in this set of samples, suggesting its corrosion speed is most fast. The pH value of the sample of the annealed AZ31 coated with polypeptide F1 coating is significantly higher than the sample of the AZ31 coated with polypeptide F3 coating within the first 48 hours. It is suggested that its corrosion speed in this process is always faster than the sample of the AZ31 coated with the F3 coating. At the 48 hours, its pH value may be in turn lower than the sample of the AZ31 coated with the F3 coating, which may be resulted from the slight bacterial pollution, and this does not suggest that in the later period its corrosion speed is slower than the latter. Therefore, it is obvious that the sample of the annealed AZ31 coated with the F3 coating has the slowest corrosion speed in the whole process, and the sample of the annealed AZ31 coated with the F1 coating also has a corrosion speed significantly smaller than that of the sample of bare metal annealed AZ31. Therefore, both of the two polypeptide coatings significantly inhibits the release of the metal ions into the DMEM solution, thereby inhibiting the corrosion and significantly increase the corrosion resistance of the material.

With reference to Table 4, the observation results for sample weights are as follows.

Figure 15:
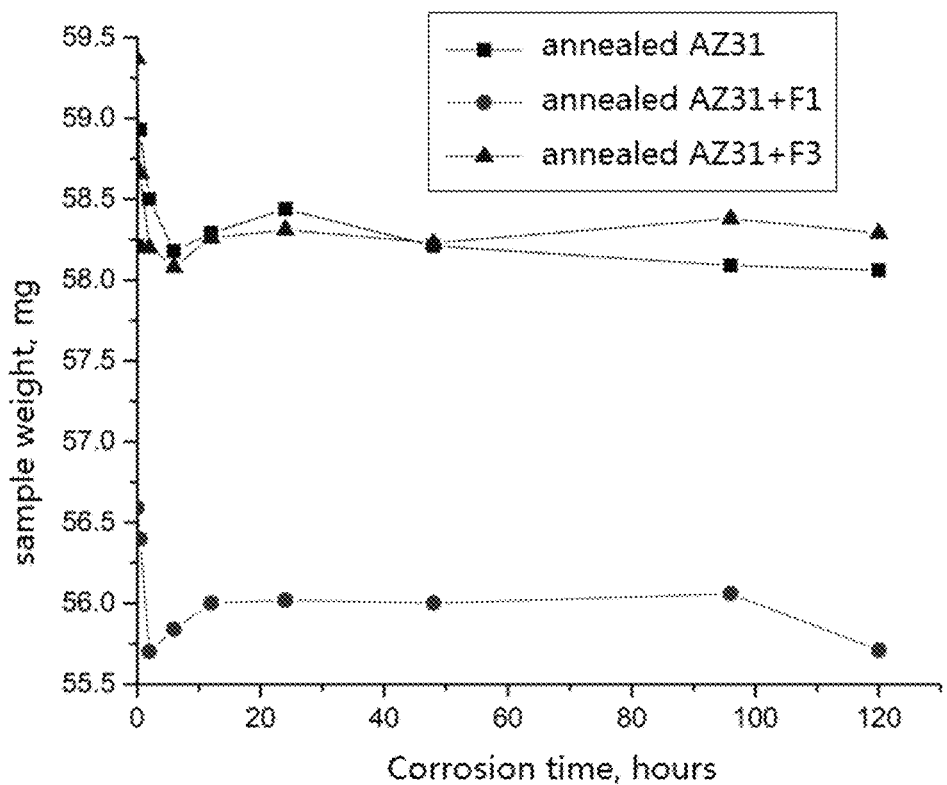
FIG. 15 shows the change analysises of weights of samples in the in-vitro corrosion experiments.

As shown in FIG. 15, the analysis for the weights of samples in the corrosion process shows obvious weight-decreasing process of three samples in the first 12 hours and the significant decrease in the weight of the sample of the bare metal annealed AZ31 after 12 hours, which is in consistent with the change of pH value. As the corrosion speed is accelerated, the weight loss of sample is aggravated. While the changes of the weights of the samples of the annealed AZ31 coated with the two polypeptides are not significant within 100 hours, especially, the change of the weight of the sample of the annealed AZ31 coated with the polypeptide F3 is still not significant at 120 hours. Thus, the observation result for changes of sample weights is consistent with the change of pH values: they suggests the materials coated with the two polypeptides can effectively inhibit the corrosion of the material.

(III) Surface Morphology and EDS Analysis of Corroded Sample (1) after the 120 hours of in-vitro corrosion experiments are finished, the samples are washed with phosphate buffer saline PBS solution (Phosphate buffer saline) for 3 to 5 minutes and dried in the bio-safety fume cupboard.

(2) The two metal samples uncoated with the polypeptide (annealed AZ31 and cold-drawn AZ31) are fixed onto sample holders by using double-layer conductive tapes carbon tape specifically used for the electron microscope. The sample with the surface coated with the polypeptide coating thereon has a poor electrical conductivity, so the surface of the sample is sprayed with carbon and then fixed on the sample holder by using the double-layer conductive tape before the electron microscope observation.

(3) The EDS analysis and the observation of the surface morphology are performed on the surface of the sample by using the scanning electron microscope JEOL 6010 SEM. Two components are selected to be analyzed: the change of the polypeptide coating on the surface can be learned from the analysis for the carbon element C component, and the corrosion situation of the magnesium alloy can be learned from the analysis for the magnesium oxide MgO component.

TABLE 5

EDS analysis for surface of corroded sample

| component | sample (%) | | |
| --- | --- | --- | --- |
| | Annealed magnesium alloy AZ31 | Annealed AZ31coated with F1 coating | Annealed AZ31coated with F3 coating |
| C | 20.33 | 59.9 | 44.3 |
| MgO | 19.45 | 12.63 | 8.85 |

The SEM surface morphology analysis suggests the following.

Figure 12:
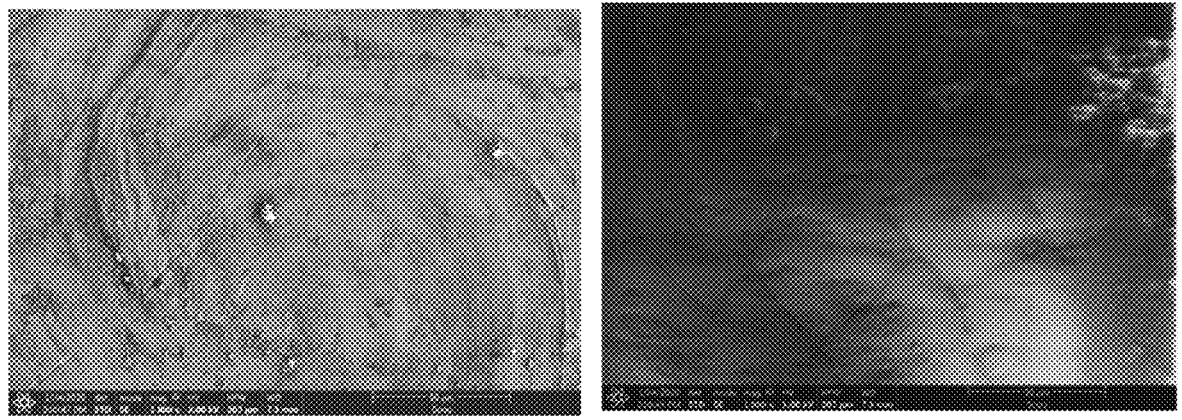
FIG. 12 shows scanning electron microscope (SEM) pictures of surfaces of samples before corrosion experiments, wherein A shows the original surface morphology of metal AZ31, and B shows the surface morphology of the magnesium alloy AZ31 coated with the polypeptide coating.
Figure 13:
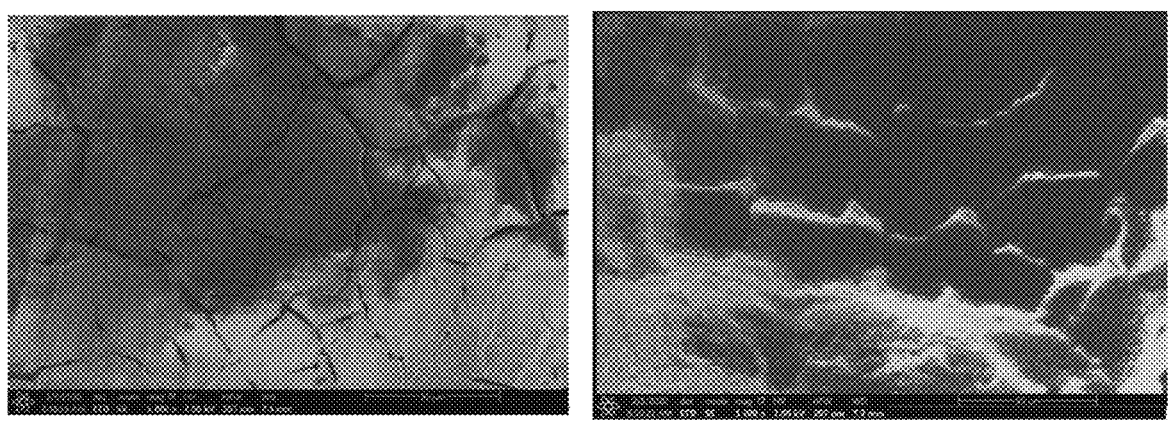
FIG. 13 shows SEM pictures of surface morphologies after 120 hours of in-vitro corrosion experiments, wherein A shows the surface of metal uncoated with the polypeptide coating after 120 hours of corrosion, B shows the surface morphology of the annealed magnesium alloy AZ31 coated with the polypeptide F1 coating after 120 hours of in-vitro corrosion, and C shows the surface morphology of the annealed AZ31 coated with the polypeptide F3 coating after 120 hours of in-vitro corrosion.
Figure 13:
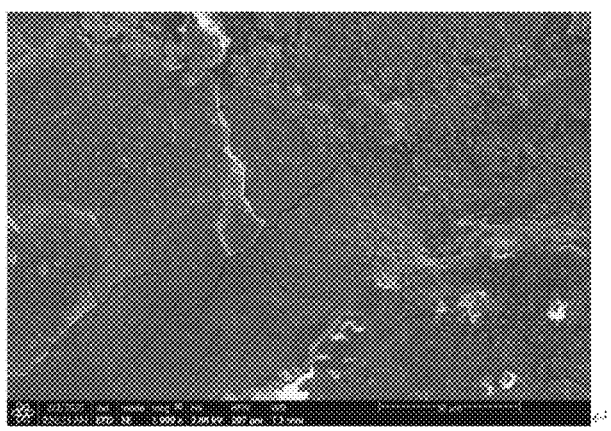

After 120 hours of in-vitro corrosion, large crack phenomenon occurs on the surface of the annealed AZ31 sample (FIG. 13). Whereas no such phenomenon occurs on the AZ31 coated with the two polypeptides, with the surface morphologies not too different from the surfaces before the corrosion (FIGS. 12 and 13). This suggests that the corrosion processes of those two materials coated with the coatings is not significant.

The EDS analysis result suggests the following.

Figure 16:
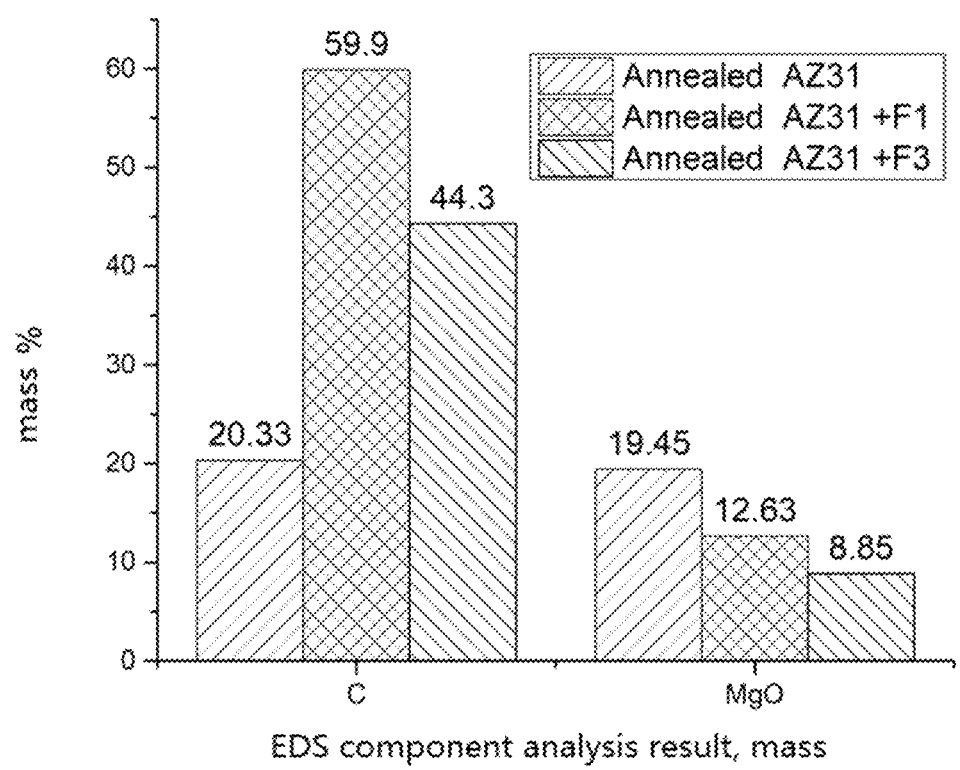
FIG. 16 shows energy dispersive spectroscopy (EDS) analysis results.

Two components, carbon and magnesium oxide, are selected to be analyzed. This is because that the polypeptide contains the carbon element and the situation of the polypeptide coating can be estimated by detecting the change of the carbon element. The product of the corrosion of the magnesium alloy is the magnesium oxide, so the corrosion situation of the material can be estimated from the another aspect by analyzing the change in the magnesium oxide component. From FIG. 16, it can be seen that after 120 hours of in-vitro corrosion, the sample of the annealed AZ31 coated with the F3 coating produces fewest magnesium oxide, followed by the sample of the annealed AZ31 coated with the F1 polypeptide coating, and the bare metal anneal AZ31 produces most magnesium oxide. Therefore, it is obvious that the corrosion of the bare metal anneal AZ31 is fastest, followed by the annealed AZ31 coated with the F1 coating, the corrosion of the sample of the annealed AZ31 coated with the F3 polypeptide coating is slowest. This suggests that the two coatings can effectively decrease the corrosion speed of the magnesium alloy.

Moreover, it can be found that the carbon content of the AZ31 coated with the F1 polypeptide coating is significantly higher than that coated with the F3 coating, suggesting that the amount of the F1 polypeptide coating is larger than the F3 polypeptide coating. This suggests from the another aspect that the F3 polypeptide coating coated on the metal surface can inhibit the corrosion of the metal material more effectively than the F1 polypeptide coating.

For the method in the Example 2, the process is simple, the operation is convenient, the implementability is high, the new material formed is stable and can be combined with other material to form a stable structure; the activity of the combined product can be maintained and enhanced; the energy consumption is small, it is easy to produce with short period and easy to be industrialized, and there is no pollution for environment.

The small-peptide-coated magnesium-based alloy biomaterial manufactured in the Example 2 has good biological activity and human body compatibility, and can be applied in the manufacture of the hard-tissue defect repair material. It can be widely used in artificial prosthesis, implantable replacement material repair of open trauma of human tissue, intraoral dental implant, repair of damage of tissue in body, and manufacture of human biomaterial such as biological catheter, joint bowl, and tubular joint nail.

The above-described are only better and implementable embodiments of the present disclosure and not intended to limit the scope of the present application. All equivalent structural changes made by using the contents of the specification and the accompanying drawings of the present application are included in the scope of the present application.

What is claimed is:

1. A heat treatment method for improving the mechanical property and the biofunctional stability of a magnesium alloy, comprising steps of:
    (1) fully annealing an original cold-drawn magnesium alloy AZ31 in an interference-free atmosphere;
    (2) polishing a surface of the magnesium alloy AZ31 from the step (1) by a waterproof abrasive paper to remove an original oxide layer while maintaining or improving the finish of the surface;
    (3) heating the magnesium alloy AZ31 obtained from the step (2) in an interference-free atmosphere created by an inert gas or a vacuum, wherein the magnesium alloy AZ31 is heated to a temperature of 330° C. to 350° C. in the interference-free atmosphere and then the temperature is kept for 3 to 4 hours;
    (4) cooling the magnesium alloy AZ31 obtained from the step (3) to room temperature, to obtain an equiaxed crystal structure which is texture-even and isotropic.

2. The heat treatment method of claim 1, wherein the polishing the surface of the magnesium alloy AZ31 by the waterproof abrasive paper comprises initial polishing and finishing; the initial polishing is performed with a 400-mesh waterproof abrasive paper for 1 to 3 minutes to remove the original oxide layer, and then the finishing is immediately performed, wherein the finishing is performed with a 1200-mesh to 2400-mesh waterproof abrasive paper for 2 to 5 minutes, to keep the finish of the surface of the magnesium alloy AZ31.

3. The heat treatment method of claim 2, wherein the initial polishing comprises grinding along one direction, with a strength effective to remove the oxide layer, the initial polishing is performed until the dark oxide layer on the surface of the magnesium alloy AZ31 is fully removed to expose the silver white magnesium metal itself, and a grinding direction in the finishing is perpendicular to the direction of the initial polishing, with a strength smaller than that in the initial polishing, until there is no scratch on the surface of the magnesium alloy AZ31.

4. A method for manufacturing a small-peptide-coated biomaterial comprising steps of: ultrasonically cleaning a magnesium alloy AZ31 to remove impurities on the surface of the magnesium alloy AZ31; dissolving polyurethane with chloroform, and then placing the cleaned magnesium alloy AZ31 into the chloroform solution dissolved with the polyurethane, so that the magnesium alloy AZ31 is fully enclosed in the solution; taking out the magnesium alloy AZ31, and letting the magnesium alloy AZ31 stand until the solution on the surface thereof is solidified; and then activating the polyurethane coated on the surface of the magnesium alloy AZ31 by using a click reaction in a plasma reactor; and finally placing the surface-activated polyurethane-coated magnesium alloy AZ31 into a sodium phosphate solution dissolved with polypeptide and applying vibration to allow them fully react to form the corresponding polypeptide coating.

5. The method of claim 4, wherein the magnesium alloy AZ31 is an original cold-drawn magnesium alloy AZ31, or the magnesium alloy AZ31 is provided by the following steps before the ultrasonically cleaning:
    (1) fully annealing an original cold-drawn magnesium alloy AZ31 in an interference-free atmosphere;
    (2) polishing a surface of the magnesium alloy AZ31 from the step (1) by a waterproof abrasive paper to remove an original oxide layer while maintaining or improving the finish of the surface;
    (3) heating the magnesium alloy AZ31 obtained from the step (2) in an interference-free atmosphere created by an inert gas or a vacuum, wherein the magnesium alloy AZ31 is heated to a temperature of 330° C. to 350° C. in the interference-free atmosphere and then the temperature is kept for 3 to 4 hours;
    (4) cooling the magnesium alloy AZ31 obtained from the step (3) to room temperature, to obtain an equiaxed crystal structure which is texture-even and isotropic.

6. The method of claim 4, wherein in the ultrasonically cleaning, the cleaning is performed for 3 to 5 minutes, and the cleaning liquid is pure water or 80% ethyl alcohol, to remove impurities on a surface of the magnesium alloy AZ31 and keep the surface of the magnesium alloy AZ31 clean.

7. The method of claim 4, wherein the chloroform solution of polyurethane is a uniform, colourless, transparent, and viscous solution formed by mixing the white solid polyurethane with colourless and transparent chloroform solution having a purity not less than 99.5% in a ratio of 3 g:100 ml and then being vibrated and stirred at a normal temperature.

8. The method of claim 7, wherein the magnesium alloy AZ31 is placed into the chloroform solution of polyurethane, fully immersed for 60 minutes, and intermittently vibrated and stirred.

9. The method of claim 4, wherein in the solidification of the solution on the surface of the magnesium alloy AZ31, the chloroform is quickly volatilized so that one uniform, dense, and stable polyurethane coating is formed on the metal surface.

10. The method of claim 9, wherein the magnesium alloy AZ31 with the solution on its surface solidified is surface-treated with oxygen plasma at 2.45 GHz for 1 minute in the plasma reactor and then stands in the atmospheric environment for 15 minutes to further promote the formation of peroxide groups and hydroxyl groups on the surface.

11. The method of claim 10, wherein after the further promoting the formation of peroxide groups and hydroxyl groups on the surface, the magnesium alloy AZ31 is moved back into the plasma reactor, the vacuum degree is adjusted to 26.7, acrylic acid vapor is slowly introduced until reaching 66.7 Pa, after reacting for 1 minute, the magnesium alloy AZ31 is taken out and cleaned for 10 minutes in an ultrasonic cleaner, thereafter, the magnesium alloy AZ31 is transferred into a mixed aqueous solution, with pH of 5.0, of 1.25 mg/ml N-hydroxysuccinimide and 5 mg/ml 1-ethyl-3-(3-dimethylaminopropyl) carbodiimide, vibrated and stirred for 20 hours at 4° C., and then taken out, finally, the polyurethane coated on the surface of the magnesium alloy AZ31 is activated.

12. The method of claim 11, wherein the sodium phosphate solution of polypeptide is a 5 mM uniform solution prepared by dissolving F3 with a purity greater than 95% into 0.1 M sodium phosphate solution.

13. The method of claim 12, wherein the surface-activated polyester-coated magnesium alloy AZ31 is placed into the sodium phosphate solution of polypeptide, taken out after 20 hours of vibration, ultrasonically cleaned in ultrapure water for 10 minutes for twice and dried so that the manufacturing is completed.

14. An application of a small-peptide-coated biomaterial, wherein the small-peptide-coated biomaterial is applied in the manufacture of a hard-tissue defect repair material, and the small-peptide-coated biomaterial is manufactured by the following steps:

ultrasonically cleaning a magnesium alloy AZ31 to remove impurities on the surface of the magnesium alloy AZ31; dissolving polyurethane with chloroform, and then placing the cleaned magnesium alloy AZ31 into the chloroform solution dissolved with the polyurethane, so that the magnesium alloy AZ31 is fully enclosed in the solution; taking out the magnesium alloy AZ31, and letting the magnesium alloy AZ31 stand until the solution on the surface thereof is solidified;

and then activating the polyurethane coated on the surface of the magnesium alloy AZ31 by using a click reaction in a plasma reactor; and finally placing the surface-activated polyurethane-coated magnesium alloy AZ31 into a sodium phosphate solution dissolved with polypeptide and applying vibration to allow them fully react to form the corresponding polypeptide coating.

15. The application of claim 14, wherein the small-peptide-coated biomaterial is applied in the manufacture of a bone fixation material.

* * * * *